(12) United States Patent
Chen

(10) Patent No.: US 8,092,377 B2
(45) Date of Patent: Jan. 10, 2012

(54) ENDOSCOPE LIGHT INTENSITY CONTROLLER

(75) Inventor: Ga-Lane Chen, Santa Clara, CA (US)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 1014 days.

(21) Appl. No.: 12/024,949

(22) Filed: Feb. 1, 2008

(65) Prior Publication Data

US 2009/0024000 A1    Jan. 22, 2009

(30) Foreign Application Priority Data

Jul. 17, 2007   (CN) .......................... 2007 1 0201087

(51) Int. Cl.
*A61B 1/06* (2006.01)

(52) U.S. Cl. ..................... 600/180; 348/69; 600/182
(58) Field of Classification Search .............. 362/552, 362/554, 558, 574; 385/117, 119; 600/180, 600/182; 348/68, 69
See application file for complete search history.

(56) References Cited

U.S. PATENT DOCUMENTS

| 5,331,949 A * | 7/1994 | Funakoshi et al. ............ 600/109 |
| 6,254,531 B1 * | 7/2001 | Higuchi et al. ............... 600/178 |
| 6,456,769 B1 * | 9/2002 | Furusawa et al. ............. 385/117 |
| 6,501,551 B1 | 12/2002 | Tearney et al. |

FOREIGN PATENT DOCUMENTS

JP    62-167471    10/1987

* cited by examiner

*Primary Examiner* — John P Leubecker
*Assistant Examiner* — Christopher Sponheimer
(74) *Attorney, Agent, or Firm* — Altis Law Group, Inc.

(57) ABSTRACT

An endoscope device includes an optical coupler, an image pickup module, a second bundle of optical fibers, a photodetector and an image processing module. The optical coupler has an input end optically coupled to a light source, a first output end and a second output end. The image pickup module includes a lens module and a first bundle of optical fibers. A end of the first bundle of the optical fibers is optically coupled to the output end of the optical coupler. An opposite end of the first bundle of the optical fibers is configured for emitting the light to illuminate an object. The second bundle of optical fibers has a end optically coupled to an image side of the lens module. An opposite end of the second bundle of the optical fibers and the second output end of the optical coupler are optically coupled to the photodetector.

10 Claims, 1 Drawing Sheet

ENDOSCOPE LIGHT INTENSITY CONTROLLER

BACKGROUND

1. Field of the Invention

The invention relates generally to endoscope devices, and more particularly to an endoscope device with a smaller image pickup module.

2. Description of Related Art

Endoscopes are a minimally invasive medical instrument used to examine the interior of a bodily organ or performing minor surgery. The instrument may have a rigid or flexible tube for insertion into the body.

Currently, endoscopes devices can be classified as electronic, ultrasonographic, or optical according to their operating principle. Applications of electronic endoscopes can be found in an article entitled "Electronic endoscope system for shape measurement" by Kazuhide et al. published at 16th international conference on pattern recognition. However, the contrast of the image captured by the conventional endoscope device is unsatisfactory, which results in a lower quality image captured by the endoscope device.

What is needed, therefore, is an endoscope device that can provide better image contrast.

SUMMARY

An endoscope device is provided. In one present embodiment, the endoscope device includes an optical coupler, an image pickup module, a second bundle of optical fibers, a photodetector, and an image processing module. The optical coupler has an input end, a first output end, and a second output end, the input end being optically coupled to a light source. The image pickup module includes a lens module and a first bundle of optical fibers. A first end of the first bundle of the optical fibers is optically coupled to the first output end of the optical coupler. An opposite second end of the first bundle of the optical fibers is configured for emitting light to illuminate an object. The second bundle of optical fibers has a first end optically coupled to an image side of the lens module and an opposite second end. The second end of the second bundle of the optical fibers and the second output end of the optical coupler are optically coupled to the photodetector. The photodetector is configured for converting light into analog electrical signals. The image processing module is configured for converting the analog electrical signals into image signals.

Advantages and novel features of the present endoscope device will become more apparent from the following detailed description of preferred embodiments when taken in conjunction with the accompanying drawings.

BRIEF DESCRIPTION OF THE DRAWINGS

The components in the drawing are not necessarily drawn to scale, the emphasis instead being placed upon clearly illustrating the principles of the present invention.

The drawing is a schematic view of an endoscope device, shown partly in cross-section and partly in block form, together with an object to be examined in accordance with a preferred embodiment of the present invention.

Corresponding reference characters indicate corresponding parts. The exemplifications set out herein illustrate at least one preferred embodiment of the present endoscope device, in one form, and such exemplifications are not to be construed as limiting the scope of the invention in any manner.

DETAILED DESCRIPTION OF THE EMBODIMENTS

Figure 1:
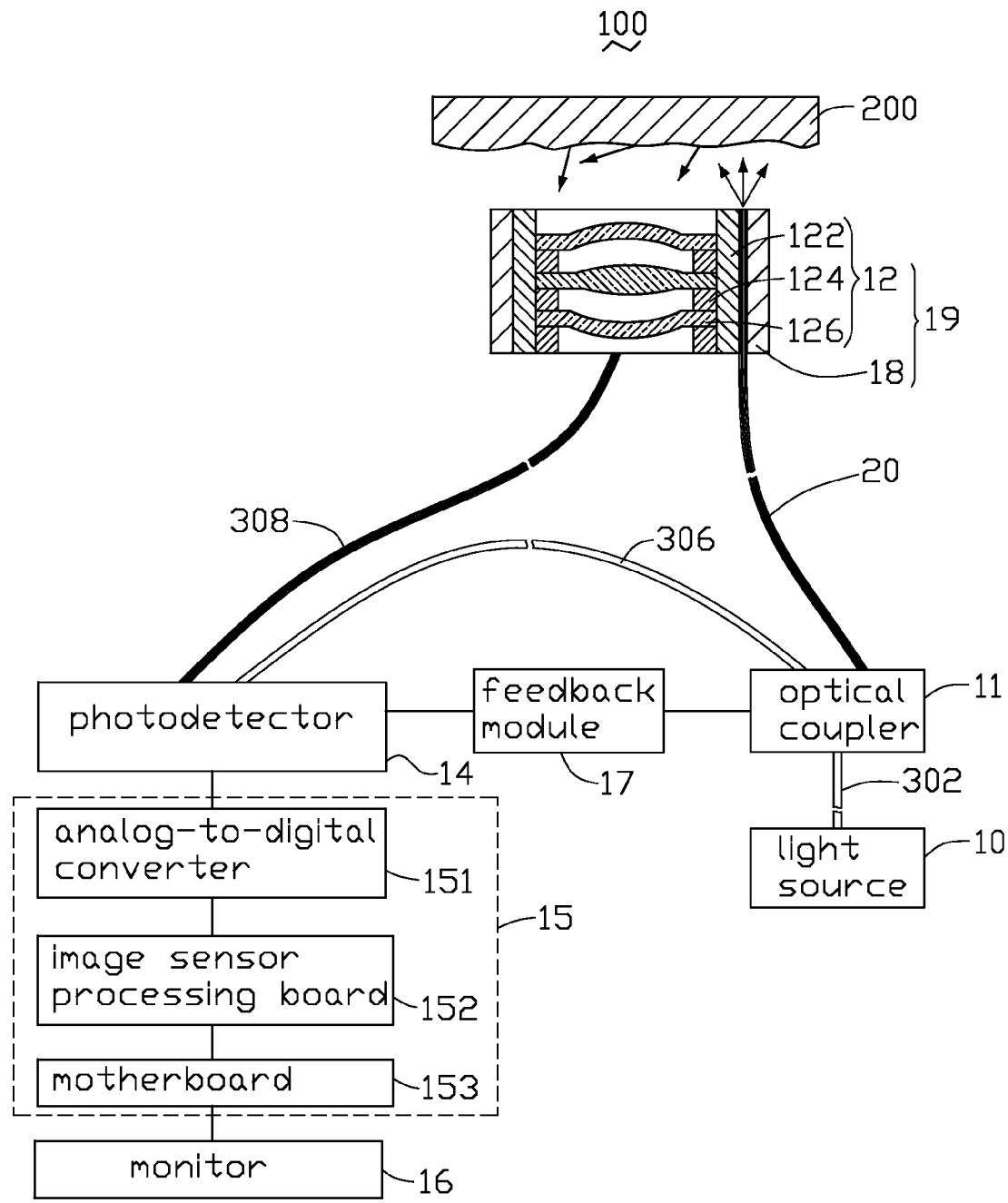

Reference will now be made to the drawings to describe embodiments of the present endoscope device in detail.

Referring to drawing, an endoscope device 100 in accordance with a present embodiment, is shown. The endoscope device 100 includes a light source 10, an optical coupler 11, an image pickup module 19, a photodetector 14, an image processing module 15, a monitor 16, and a feedback module 17. Included, as an example, is an object 200 for examination with the endoscope 100.

The image pickup module 19 includes a tube 18, a lens module 12, and a first bundle of optical fibers 20. The lens module 12 is accommodated in the tube 18.

The light source 10 is optically coupled to an input end of the optical coupler 11 through a first optical fiber 302. A first end of the first bundle of the optical fibers 20 is optically coupled to a first output end of the optical coupler 11. A second output end of the optical coupler 11 connects with the photodetector 14 through a second optical fiber 306. An opposite second end of the first bundle of the optical fibers 20 is configured for emitting the light to illuminate an object.

A second bundle of optical fibers 308 has a first end optically coupled to an image side of the lens module 12 and an opposite second end. The photodetector 14 connects with the second end of the second bundle of the optical fibers 308 and the second output end of optical coupler 11 being optically coupled thereto. The photodetector 14 is configured for converting the light into analog electrical signals. The image processing module 15 includes an analog-to-digital converter 151 for converting the analog electrical signals into digital electrical signals, an image sensor processing board 152 for creating the image signals associated with the object using the digital electrical signals and a motherboard 153. The analog-to-digital converter 151 connects with the image sensor processing board 152. The image sensor processing board 152 connects with the motherboard 153. The photodetector 14 connects with the analog-to-digital converter 151 of the image processing module 15. The motherboard 153 of the image processing module 15 connects with the monitor 16. The feedback module 17 interconnects the photodetector 14 with the optical coupler 11.

The optical coupler 11 is configured to split the light received from the light source 10 into two portions and couple the two portions of light to the first output end and the second output end respectively. The light intensity ratio of the two portions of the light is adjustable according to design or practical requirement. For example, if l is designated as the total energy of the received light, the energy levels of the light portion coupled to the first output end and the second output end are a %×l and b %×l, wherein a %+b %=100%. In the present embodiment, the parameter of the optical coupler 11 is adjustable to change the intensity ratio of a and b.

The lens module 12 includes a plurality of lenses 126 and a barrel 122 receiving the lenses therein. The diameter of the lens barrel 122 is in an approximate range from 0.2 mm to 8 mm. Advantageously, the diameter of the lens barrel 122 is in an approximate range from 1 mm to 3 mm. The first bundle of the optical fibers 20 extends through the barrel 122. In the present embodiment, at least one of the lenses 126 has an aspherical surface configured for reducing image aberration. The amount of the lens 126 is three. Each of the lenses 126 are separated from each other by spacer 124. The diameter of each of the lenses 126 is in an approximate range from 0.2 mm to 8 mm. Preferably, the diameter of each of the lenses 126 is in an approximate range from 0.5 mm to 2 mm. The thickness of each of the lenses 126 is in an approximate range from 0.4 mm to 1.6 mm. Preferably, the thickness of each of the lenses 126 is in an approximate range from 0.8 mm to 1.2 mm. Thus, the lens 126 has smaller size thereby reducing the size of the lens module 12. The image pickup module 19 being smaller facilitates insertion into the object 200 more conveniently. The upper surface and bottom surface of the lens 126 have anti-reflection film (not shown in FIG. 1) coated thereon. The lens 126 has high transmittance for light in the spectrum visible to humans. For example, the transmittance of the lens 126 at wavelengths from 400 nm to 670 nm is over 95%.

The feedback module 17 is configured for adjusting the parameter of the optical coupler 11 to change the intensity ratio of the light coupled to the first output end and the second output end of the optical coupler 11 according to the signal of the photodetector 14. By optimizing the intensity ratio of light, a sensitivity of the photodetector 14 and contrast of the image captured by the photodetector 14 can be improved. Thus, images with higher quality can be obtained and displayed by the monitor 16.

In use, the image pickup module 19 is inserted into the object 200 (such as stomach) for examination thereof. The light source 10 is turned on and provides light to the optical coupler 11. The optical coupler 11 splits the light into a first light beam and a second light beam. The first light beam is transmitted to the photodetector 14 via the second optical fiber 306 and serves as a reference light for the photodetector 14. The second light beam is transmitted to illuminate the object 200 via the first bundle of lighting fibers 20 and then is transmitted to the lens module 12 by way of reflection or scattering. The lens module 12 collects the light transmitted to the photodetector 14 via the second bundle of optical fibers 308. The photodetector 14 is configured for converting the light into analog electrical signals. The image processing module 15 is configured for converting the analog electrical signals into image signals associated with the object 200. The image ultimately displayed by the monitor 16 for examination. Thus, the user can see inside the object 200.

The endoscope device 100 in accordance with a present embodiment, includes an optical coupler 11. The second output end of optical coupler 11 is connected with the photodetector 14 through the second optical fiber 306. The first light beam goes through the second output end of the optical coupler 11. The first light beam is used to be the reference point of the photodetector 14, which can improve contrasts of the image.

Finally, it is to be understood that the above-described embodiments are intended to illustrate rather than limit the invention. Variations may be made to the embodiments without departing from the spirit of the invention as claimed. The above-described embodiments illustrate the scope of the invention but do not restrict the scope of the invention.

What is claimed is:

1. An endoscope device, comprising:
   an optical coupler having an input end, a first output end and a second output end, the input end being optically coupled to a light source;
   an image pickup module comprising a lens module and a first bundle of optical fibers, a first end of the first bundle of the optical fibers being optically coupled to the first output end of the optical coupler, an opposite second end of the first bundle of the optical fibers being configured for emitting the light to illuminate an object;
   a second bundle of optical fibers having a first end optically coupled to an image side of the lens module and an opposite second end;
   a photodetector with the second end of the second bundle of the optical fibers and the second output end of optical coupler being optically coupled thereto, the photodetector being configured for converting the light into analog electrical signals; and
   an image processing module configured for converting the analog electrical signals into image signals associated with the object.

2. The endoscope device as claimed in claim 1, further comprising the light source optically coupled to the input end of the optical coupler.

3. The endoscope device as claimed in claim 1, wherein the image processing module includes an analog-to-digital converter for converting the analog electrical signals into digital electrical signals, an image sensor processing board for creating the image signals associated with the object using the digital electrical signals.

4. The endoscope device as claimed in claim 1, wherein the image pickup module includes a plurality of lenses and a barrel receiving the lenses therein.

5. The endoscope device as claimed in claim 4, wherein the diameter of the lens barrel is in an approximate range from 0.2 mm to 8 mm.

6. The endoscope device as claimed in claim 1, wherein the intensity ratio of the output light of the first output end to the second output end of the optical coupler is adjustable.

7. The endoscope device as claimed in claim 1, wherein the optical coupler comprises a feedback module, the feedback module interconnecting the photodetector with the optical coupler, the feedback module being configured for adjusting the intensity ratio of the output light of the optical coupler.

8. The endoscope device as claimed in claim 4, wherein the first bundle of the optical fibers extending through the barrel.

9. The endoscope device as claimed in claim 8, wherein at least one of the lenses has an aspherical surface.

10. The endoscope device as claimed in claim 9, wherein the diameter of each of the lenses is in an approximate range from 0.2 mm to 8 mm.

* * * * *